United States Patent
Basaganas Millan

(10) Patent No.: US 6,354,513 B1
(45) Date of Patent: Mar. 12, 2002

(54) PLUG FOR CONTAINERS OF EVAPORABLE LIQUIDS

(75) Inventor: Jordi Basaganas Millan, Barcelona (ES)

(73) Assignee: DRK Espana, S.A., Barcelona (ES)

( * ) Notice: Subject to any disclaimer, the term of this patent is extended or adjusted under 35 U.S.C. 154(b) by 0 days.

(21) Appl. No.: 09/673,524
(22) PCT Filed: Feb. 11, 2000
(86) PCT No.: PCT/ES00/00048
  § 371 Date: Oct. 13, 2000
  § 102(e) Date: Oct. 13, 2000
(87) PCT Pub. No.: WO00/48922
  PCT Pub. Date: Aug. 24, 2000

(30) Foreign Application Priority Data

Feb. 15, 1999 (ES) .................................. 9900299

(51) Int. Cl.[7] ................................................ A61L 9/03
(52) U.S. Cl. ........................ 239/44; 239/47; 215/355
(58) Field of Search ............................. 215/14, 26, 28, 215/355, 364, 274, 275, 231; 220/315, 787, 789, 790, 801, 802, DIG. 19; 239/44–51.5

(56) References Cited

U.S. PATENT DOCUMENTS

| | | | | |
|---|---|---|---|---|
| 3,028,100 A | * | 4/1962 | Xenakis et al. | 239/47 |
| 3,207,441 A | * | 9/1965 | Schreiber | 239/47 |
| 3,724,756 A | * | 4/1973 | Maltenfort | 239/44 |
| 4,739,928 A | * | 4/1988 | O'Neil | 239/45 |
| 5,669,767 A | | 9/1997 | Bureau et al. | |
| 5,725,152 A | * | 3/1998 | Akyu | 239/45 |

FOREIGN PATENT DOCUMENTS

| | | |
|---|---|---|
| EP | 0740941 A1 | 11/1996 |
| ES | 2050332 T3 | 5/1994 |
| FR | 2724632 A1 | 3/1996 |
| GB | 266054 | 10/1993 |
| WO | WO 00/48922 | 8/2000 |

* cited by examiner

Primary Examiner—Nathan J. Newhouse
(74) Attorney, Agent, or Firm—Rosenman & Colin LLP

(57) ABSTRACT

The plug comprises a body (1) permanently coupled to the neck of a container for an air freshener or insect repellent liquid, with evaporation occurring through a wick (11) axially coupled in a concentric passage of the plug itself. An inner part of the axial passage of the plug in which wick (11) is inserted is provided with slits (7) along the main generatrix line, forming sectors (9) provided with semi pyramidal projections (12), defining means which allow motion in the direction of insertion of wick (11) and prevent its displacement in the outwards direction for removing said wick (11) from the plug, which prevents the container on which the plug is applied from being refilled with a product other than the original.

1 Claim, 2 Drawing Sheets

B-B

A-A

B-B

PLUG FOR CONTAINERS OF EVAPORABLE LIQUIDS

OBJECT OF THE INVENTION

The present invention relates to a plug for containers of liquids which are meant to be evaporated to be used as air fresheners and/or elimination of insects, or similar applications, which plug is complemented by a wick which passes trough it axially, with part of said wick submerged in the liquid contained in the container and another part emerging on the outside, through which the product contained in the container may evaporate.

The object of the invention is to provide a plug which prevents refilling the container by having means which allow an axial mounting as the wick is introduced but prevent its extraction or its reuse. That is, one of the main characteristics of the plug is that it is provided with internal elements which allow axial displacement of the wick in one sense and prevent displacement in the opposite direction, in order to prevent extraction of the wick once mounted in the plug, thereby preventing refilling of the container with a liquid other than the original, as said plug is of the type which are permanently mounted on the neck of the container, so that it cannot be separated.

BACKGROUND OF THE INVENTION

There are a number of devices or means used to evaporate air freshener liquids, whether to provide a pleasant atmosphere in a room or to fill said room with a product which attacks insects in order to eliminate them.

Among these numerous systems employed there is on in which the discharge of the liquid of the container takes place through wick mounted on a plug coupled to the neck of the container, is that one end of the wick is immersed in the liquid contained and the other end emerges out to allow the liquid to evaporate.

This type of plug may be permanently mounted on the container neck, so that it is practically impossible to remove it without breaking or deforming it, thus preventing a subsequent correct coupling of the plug on the container.

However, the wick, which is generally mounted on an axial orifice of the plug, may be easily mounted and removed, allowing the container to be refilled with a liquid other than the original once this is exhausted, resulting in a reduced safety as this new refilled liquid, other than the original, may be harmful if used as intended, such as by being inflammable, toxic, corroding plastic or electric components, etc.

Furthermore, if the wick may be separated and coupled at will on the plug a serious problem arises, namely that children may remove the wick attracted by the pleasant smell of the liquid contained, not only possibly placing the wick in their moths, with the ensuing risk as these products are often toxic, but even ingesting the contents as the wick has been removed from the plug.

A protection device is known for wicks through which evaporation of an air freshener takes place, described in Patent WO 98/00177, in which the plug is attached to a plastic cap which covers the outer part of the wick, so that the wick is well protected by said cap, preventing children from sucking it or ingesting the liquid in which the wick is soaked, and thus the cap must be removed by suitable means and by an adult in order to leave part of the wick exposed to allow evaporation of the liquid in the container on which the plug is coupled, which obviously does not eliminate the risk that once the container wick is exposed by removing the cap, a child may extract the wick and ingest the contained liquid.

DESCRIPTION OF THE INVENTION

The disclosed plug has been designed to solve the above described problems by means of a simple yet considerably effective means, based on providing means which prevent the wick from being separated or removed from the plug, thus preventing refilling the container to which said plug is applied.

More specifically, the plug of the invention, in the conventional manner, comprises an annular body with a neck directed inwards, with the top edge retained, corresponding to the container neck, with the plug mounted permanently on said container neck, with the characteristic that said plug has a concentric neck which emerges and is prolonged axially inwards, with a number of slits along the main line, which define sectors meant to embrace and press on the wick, which preferably consists of a cylindrical body which passes through said axial passage of the plug, so that the internal part with sectors which embrace and press on the lateral surface of the wick is complemented by a further concentric neck with a slightly larger diameter, also provided with slits parallel to the main line, which press on the previous ones when the plug is coupled to the container neck.

In order to prevent the wick from being extracted, that is, moved so that it is separated from the plug, the aforementioned sectors defined in the axial and inner neck which press on the lateral surface of the wick are provided with triangular, or semi-pyramidal, projections, with their vertex located in an internal or lateral surface of each sector, so that the lateral surfaces of said projections diverge inwards, defining ramps which allow the displacement of the wick in one direction but prevent motion in the opposite direction, that is, they prevent removing the wick once it is inserted in the plug except by a strong effort applied on said wick, which would cause it to break and made useless, so that the plug would be also ruined as it requires a corresponding wick to allow the contained liquid to evaporate. Thereby the main characteristic is achieved, that the plug is made unrefillable, with the ensuing advantages, such as preventing the container from being filled with a liquid other than the original and preventing children from removing the wick and ingesting the contents.

DESCRIPTION OF THE DRAWINGS

The described construction and advantages of the ramp of the invention, in accordance with an example of a preferred embodiment, may be further understood in view of the following description made with reference to the accompanying drawings where for purpose of illustration only and in no way meant as a definition of the limits of the invention the following is shown.

PREFERRED EMBODIMENT OF THE INVENTION

Figure 1:
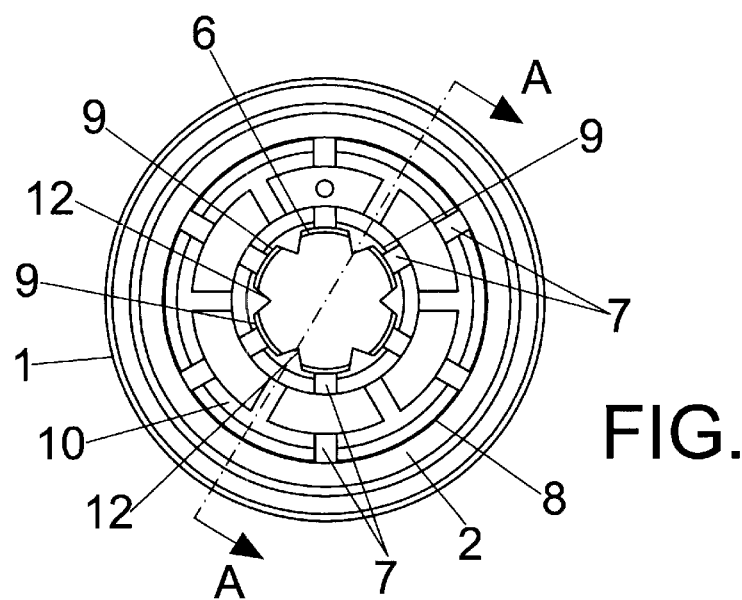
FIG. 1 shows a side elevation view of a plug for containers of evaporable liquids, according to the object of the present invention.
Figure 2:
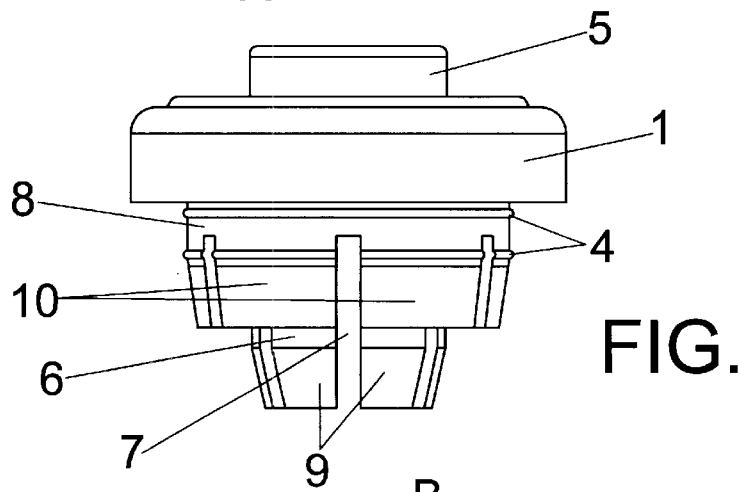
FIG. 2 is a bottom plan view of the plug of the previous figure.
Figure 3:
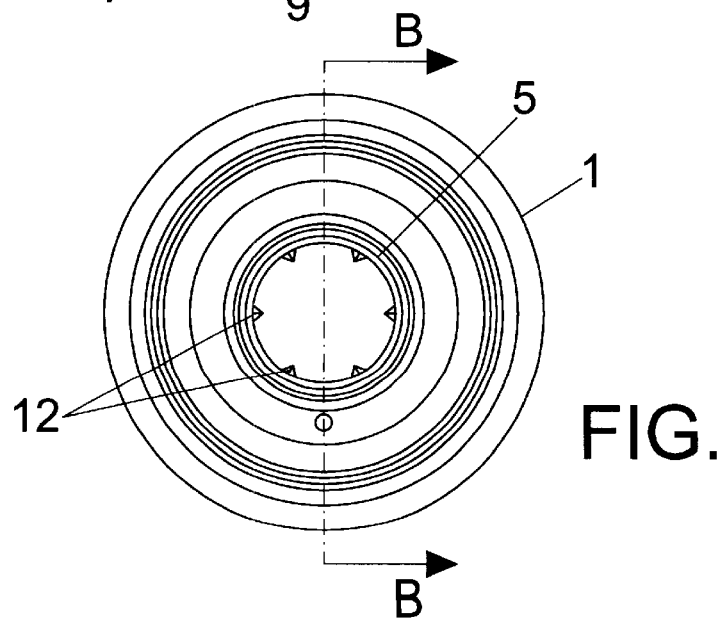
FIG. 3 is a top plan view of the plug of FIG. 1, clearly showing as in FIG. 2 the internal triangular outline projections provided in the sectors which embrace and press on the wick, through which evaporates the liquid of the container bearing the plug itself.

As may be seen in the figures the plug of the invention applicable to containers of liquids meant to be evaporated for air freshening or removal of insects, where the product has the corresponding properties, includes an annular body (1) in which is defined an internal annular neck (2) with a projection (3) directed inwards and projections (4), which determine means of coupling and retention to the corresponding neck of the container on which the plug is applied, with the characteristic that body (1) is provided with a concentric neck (5) which emerges slightly out and above the body of plug (1), while downwards, that is in the opposite direction, it is prolonged in an internal neck (6) provided with slits (7) along the main line, so that these slits of the internal and axial neck (6) are also made in wall (8), which is shorter than the length of internal neck (6), although greater in diameter, with wall or annular partition (8) and the wall of neck (6) being concentric and both provided with slits (7) along the main generatrix lines, in each case defining a sector, respectively (9) and (10).

Figure 4:
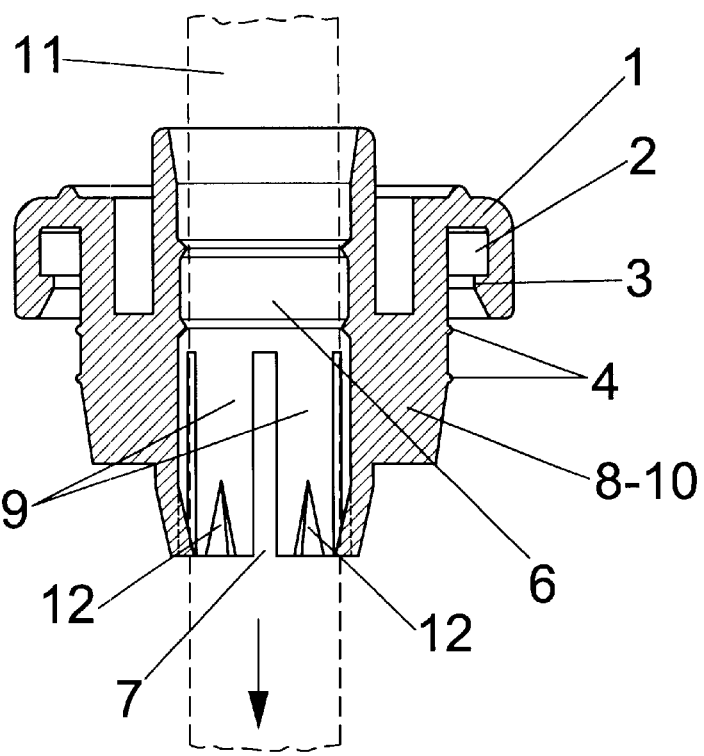
FIG. 4 is a sectional view along the line A—A of FIG. 2 with the wick coupled axially to the concentric passage defined in the plug itself.
Figure 5:
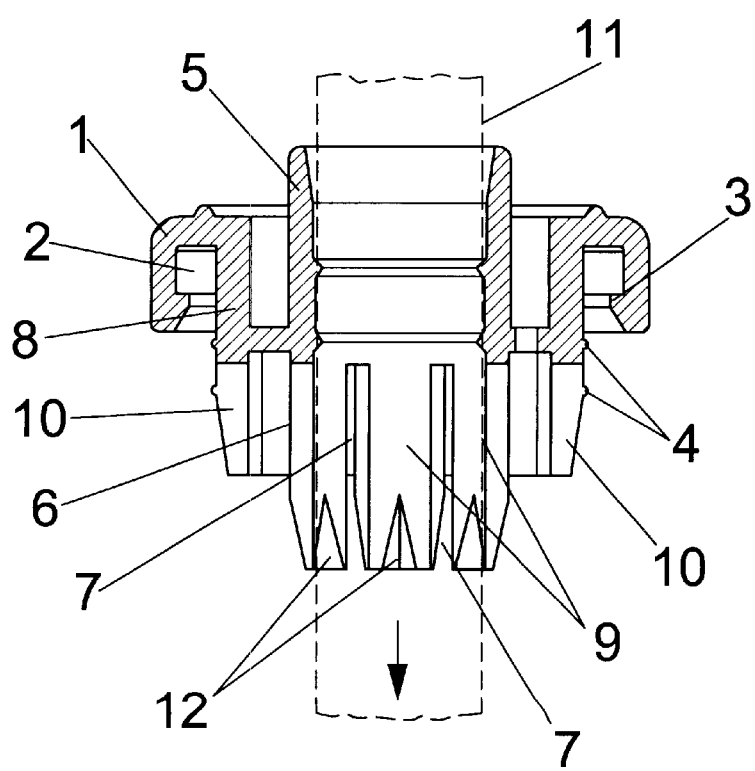
FIG. 5 shows a further sectional view in this case along the B—B line of FIG. 3, also including the wick which as can also be seen in the previous figure is free to move in the direction indicated by the arrow, but which may not move in the opposite direction, preventing said wick from being removed or separated from the plug.

Based on this construction the corresponding wick (11) which consists of a cylindrical body, is passed through the aforementioned axial concentric neck of the plug in the direction indicated by the arrows of FIGS. 4 and 5, that is, towards the inside of the container bearing the plug.

Thus, in order to prevent wick (11) from being removed, or rather to prevent it from being moved in the opposite direction, sectors (9) of concentric neck (6) which determines the axial passage, which press on wick (11), are provided with semi-pyramidal projections (12), with a triangular outline, as clearly shown in the figures, so that at the innermost area of the surface of sector (9) the projections begins with an initial zero height to then define its semi pyramidal shape, that is, increasing in width and forming a ramp which, as mentioned above, allows an inwards displacement of wick (11), and so that if said wick is extracted, moving it in the opposite direction, semi-pyramidal projections (12) will stop it, by inserting themselves in the lateral surface of wick (11) so that it cannot be removed except by breaking it, by applying a strong tension to it.

What is claimed is:

1. Plug for containers of evaporable liquids, of the type comprising an annular body with a neck for coupling and permanent attachment to the corresponding neck of the container to which it is applied, and provided with an axial concentric passage for placing a cylindrical wick, which is partially submerged in the liquid of the container and partially emerges outwards to allow evaporation through it of the liquid of the container, characterised in that the innermost or lowermost passage area of the wick comprises a concentric neck provided with slits along the main generatrix line, defining sectors which press on the lateral surface of the wick, with the neck enveloped by a second neck of greater diameter which is also provided with slits along the main generatrix line, so that the second neck is shorter than said neck; with the property that the sectors of said neck which press on the wick are provided with triangular semi-pyramidal projections which provide means to allow an inwards displacement of the wick and prevent its displacement in the opposite direction, in order to prevent it from being separated from the plug once mounted on it, and preventing refilling of the container on which said plug is applied.

* * * * *